United States Patent
Strobel et al.

(10) Patent No.: US 6,863,671 B1
(45) Date of Patent: Mar. 8, 2005

(54) BIODEGRADABLE FIXATION ELEMENT

(75) Inventors: Michael Strobel, Straubing (DE);
Andreas Weiler, Berlin (DE); Andre Timmermans, Ruurlo (NL)

(73) Assignee: Storz GmbH & Co. KG (DE)

( * ) Notice: Subject to any disclaimer, the term of this patent is extended or adjusted under 35 U.S.C. 154(b) by 386 days.

(21) Appl. No.: 09/694,845

(22) Filed: Oct. 20, 2000

(30) Foreign Application Priority Data

Oct. 21, 1999 (EP) .......................................... 99121052

(51) Int. Cl.⁷ ............................................. A61B 17/56
(52) U.S. Cl. ............................ 606/73; 606/60; 606/77
(58) Field of Search ............................ 606/60, 72, 73, 606/77

(56) References Cited

U.S. PATENT DOCUMENTS

| | | | | |
|---|---|---|---|---|
| 4,484,570 A | * | 11/1984 | Sutter et al. | 606/71 |
| 5,047,030 A | * | 9/1991 | Draenert | 606/65 |
| 5,084,050 A | | 1/1992 | Draenert | 606/77 |
| 5,129,904 A | * | 7/1992 | Illi | 606/72 |
| 5,470,334 A | * | 11/1995 | Ross et al. | 606/104 |
| 5,860,973 A | * | 1/1999 | Michelson | 606/61 |
| 5,968,047 A | * | 10/1999 | Reed | 606/69 |

FOREIGN PATENT DOCUMENTS

| | | |
|---|---|---|
| DE | 30 27 138 A1 | 12/1981 |
| EP | 0502698 B1 | 9/1992 |
| JP | 09110220 | 4/1997 |
| WO | WO 93/15694 | 8/1993 |
| WO | WO 97/37603 | 10/1997 |
| WO | WO 99/44544 | 9/1999 |

OTHER PUBLICATIONS

OP–Journal, Dec. 1998.

* cited by examiner

*Primary Examiner*—Beverly M. Flanagan
(74) *Attorney, Agent, or Firm*—St. Onge Steward Johnston & Reens, LLC

(57) ABSTRACT

A biodegradable fixation element is provided for anchoring a transplant on bone. A rigid body is made of a biodegradable material, said body having an outer side and a hollow interior surrounded by a wall of said body. Numerous perforations are provided in said wall of said body for allowing growth of bone material into said interior of said body via said numerous perforations. It is proposed that the perforations are formed between said anchoring members and said perforations are formed as holes passing through said wall of said body (FIG. 1).

3 Claims, 2 Drawing Sheets

BIODEGRADABLE FIXATION ELEMENT

BACKGROUND OF THE INVENTION

The invention relates to a biodegradable fixation element, in particular for anchoring bone implants, having a body with anchoring elements arranged on its outer side.

A biodegradable fixation element in the form of an interference screw is disclosed in OP Journal 14 (1998) pages 278–284 "Biodegradierbare Interferenzschrauben in der Kreuzbandchirurgie" A. Weiler et al., Georg Thieme Verlag Stuttgart, N.Y.

Biodegradable materials are ones which are completely absorbed by the body. They also include composite materials which are only partially taken up by the body.

Interference screws have the purpose of anchoring a tendon or ligament transplant or implant in a bone. A channel is drilled into the bone in which the transplant is inserted. The interference screw is screwed into the intermediate space between the transplant and the inner wall of the channel, so that the transplant is then clamped between the screw and the inner channel wall.

Considerable forces arise in such a transplant, for example in the cruciate ligaments in a knee joint, so that the clamping force must be correspondingly large to ensure a secure anchoring. The screw is therefore provided with anchoring elements in the form an outer threading, which penetrates into the bone material at the inside of the channel. At the same time, the outer threading engages the transplant to be anchored. To exert the considerable mechanical clamping force, the fixation element must have a certain minimal geometric size.

When the fixation element begins to degrade biologically, a correspondingly large hollow space arises. Bone material can grow into this space with time, so that the transplant remains firmly anchored. If the biological degradation does not take place parallel with the bone growth, instable conditions can arise in that the bone growth is not sufficient or is not sufficiently fixed, while hollow spaces have already arisen due degradation.

International patent application WO 99/44544 discloses a surgical implant for fixing a bone block into a drillhole in a bone. The implant has an elongated hollow body and is manufactured from a bioabsorbable polymer. At least one gripping element is provided on the elongated body for locking the implant into the drillhole. The body is provided with at least one slot extending over the overall axial length of the body. The slotted body can be squeezed into the space between the drillhole and the bone block for fixing said bone block within said drillhole. The body may be provided with pores for allowing a growth of bone material into said body.

The basic principle is to fix the rigid bone block by squeezing the slotted body between the block and the drillhole. If one has to anchor transplants of flexible material, for example a tendon, the fixation element needs to be rigid and not deformable or squeezable.

Such fixation elements are subject of the present application.

If revisions are required and a new transplant is to be applied, corresponding borings must be made for inserting the fixation element. However, if sufficient bone material is not present, these borings cannot be properly made and correspondingly the new transplant cannot be fixed.

An object of the present invention is to provide a biodegradable fixation element of the mentioned type, which allows the formation of a bone network structure in the region of the transplant.

It is a further object of the transplant of the present invention to maintain the anchoring of the transplant and the mechanical strength of said body during biodegradation as long as possible but allowing a growth of bone material into said interior of said body.

SUMMARY OF THE INVENTION

According to the present invention, these objects are achieved in that said perforations are formed between said anchoring members and said perforations are formed as holes passing through said wall of said body.

The holes instead of only pores allow a fast bone growth in a remarkable extend into the interior of the fixation element. The entire fixation body surface is covered with bone growth. When the material is reabsorbed, one obtains a bone network structure which is sufficiently stable. If a revision is necessary after unsuccessful anchoring of the transplant or after a rupture of the transplant, the network structure presents no problem in the case of a revision. Sufficient bone material is available, even if the biodegradable material is not yet completely absorbed, to not only maintain a very stable and durable anchoring of the transplant, but also to provide sufficient bone material for setting further borings.

If the bone growth is faster than the bio-absorption, material can grow into the interior space through the holes or can grow with the bone material present therein, where a stable, rigid, three-dimensional structure is built up. If the fixation element is large, the holes can be provided to pass partially or completely through the element. The form, distribution and number of perforations can be varied.

Most of the perforations are formed to be holes completely passing through a wall of a hollow body. This feature has the advantage that the perforations are simple to fabricate, while the stability of the element is still retained.

Further, the perforations are formed between the anchoring elements. That feature has the-considerable advantage that the anchoring elements can be configured to be very stable or massive to be able to exert or to receive the corresponding anchoring forces and not be weakened by the perforations. This design allows a growth of bone material via the holes into the interior simultaneously to the biodegradation of the body. The fact that the holes are not present within the anchoring elements but only between them, maintains the mechanical strength of the body and consequently the anchoring of the transplant for a long time period, during that time period a biodegradation already takes place, in particular in the area of the holes i.e. between the anchoring elements. This prolongs the mechanical anchoring of the transplant by the fixation element and simultaneously an enhanced anchoring by the grown bone material.

In a further embodiment of the present invention, the element is formed as a screw body of an interference screw and the anchoring members are formed as an outer threading. In this case, the perforations are formed between the windings of the threading. The above-mentioned advantages are achieved in such a configuration.

In a further embodiment of the present invention, the element comprises a channel completely passing through the element. The feature has the advantage that the channel having a corresponding contour can act to receive a tool for screwing in the fixation element, when configured as an interference screw. The bone material on the other hand can also grow into the open ends of the channel into the interior. In addition, bone material can be placed in the channel, for example bone slurry or bone pieces, which for example have been removed from the pelvic crest region. This bone material then grows together with the bone cells entering through the perforations to form a rigid bone composite. It is also possible to deposit anticyto-statics or antibiotics to avoid infections. Growth factors (hormones, etc.) can also be provided in the interior space. These can also be deposited on the surface of the element during fabrication or be embedded in the degradable material.

It will be understood that the above-mentioned features and those to be discussed below are applicable not only in the given combinations, but may be employed in other combinations or taken alone without departing from the scope of the present invention.

BRIEF DESCRIPTION OF THE DRAWINGS

The invention will now be described in more detail in conjunction with a selected embodiment and the attached drawings.

DETAILED DESCRIPTION OF A PREFERRED EMBODIMENT

Figure 1:
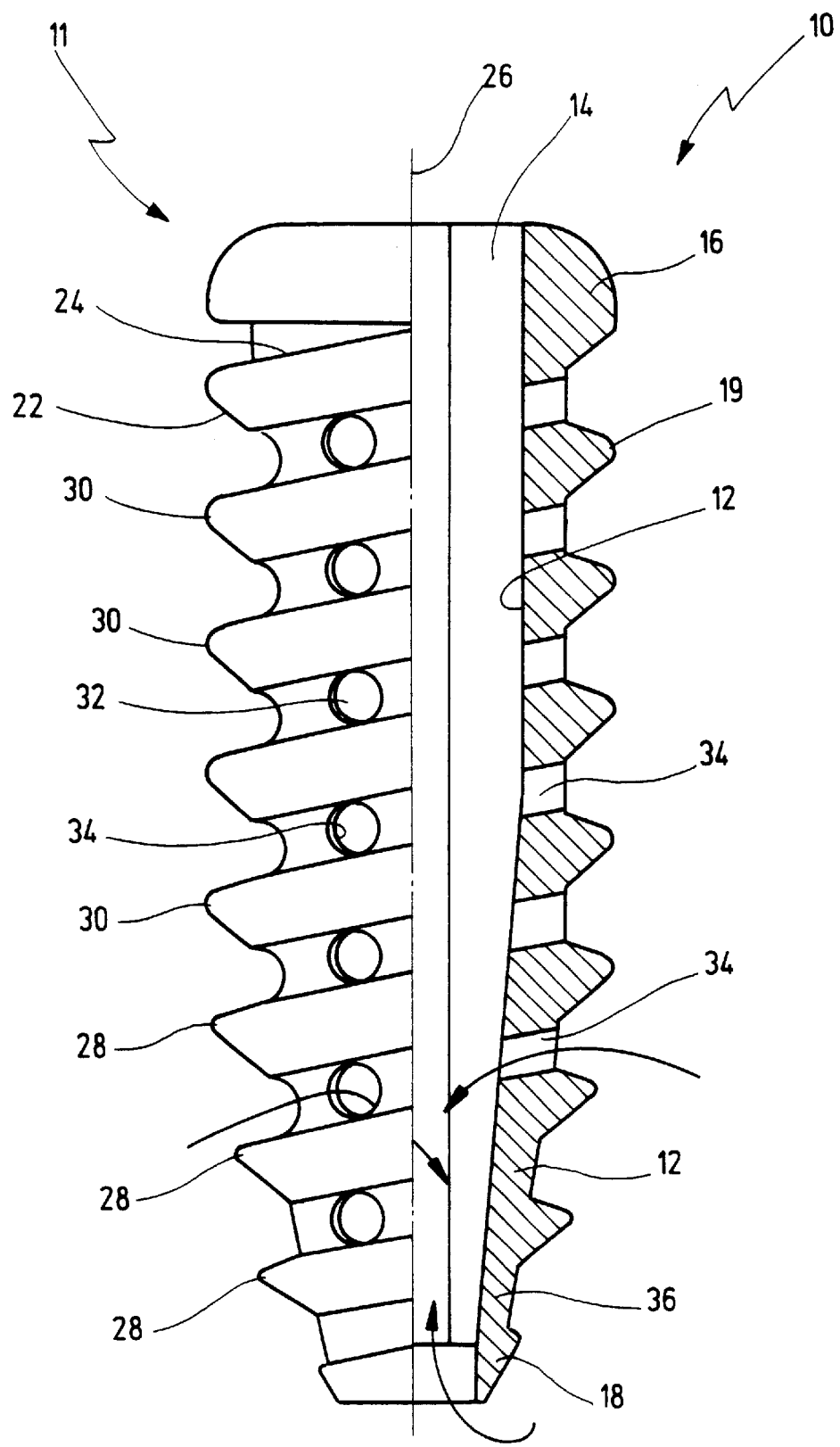
FIG. 1 shows a side view of a biodegradable fixation element according to the invention in the form of an interference screw, where the right half of the figure is shown in cross-section.

A fixation element is shown in FIG. 1 and designated generally with the reference numeral 10. The element 10 in the present embodiment is formed as an interference screw 11.

The interference screw 11 comprises a body 12 having a head end 16 and a penetrating end 18. The approximately hollow cylindrical screw body tapers in the region of the penetrating end 18. A channel 14 passes completely through the body from the head 16 to the penetrating end 18, whose cross-section at least in the region of the head 16 has a sexangular contour.

The body 12 is provided with anchoring members 19 in the form of an outer threading 20, which extends from the penetrating end 18 to the head 16. The outer threading 20 in the present embodiment is provided with a profile to be a buttress threading. The forward flanks 22 facing the penetrating end 18 have an angle of about 45 degrees with respect to the center axis 26 of the screw 11. The other flanks 24, seen from the head 16 toward the penetrating end 18, are inclined by about 15 degrees downwardly with respect to a plane perpendicular to the axis 26. In the region of the penetrating end 18 up to about the maximum core diameter of the body 12, the flanks 22 and 24 join one another in a sharp edge 28. In the following sections, the flanks 22 and 24 join one another in a blunt edge 30. A first region of the threading 20 results near the penetrating end 18 with sharp threads and a region follows extending to the head 16 with blunt threads.

The interference screw 11 consists of a biodegradable material. Examples of biodegradable materials are polycaprolactone, poly(L-lactide), polyglycol, poly(D,L-lactide), poly(D,L-lactide-co-glycol), poly(D,L-lactide-co-captrolactone), polydioxanone, copolyoxalate and polycarbonate, for example, polyglycol-co-trimethylenecarbonate and poly(glutamine-co-leucine).

The wall of the body 12 is provided with numerous perforations 32 in the form of holes 34 passing completely therethrough. The holes 34 are arranged to be located between windings of the outer threading 20.

In the region of the penetrating end 18, no perforations are provided up until the first complete winding, since the body 12 is tapered in this region and unnecessary weakening in this region could result from the perforations. In the further region, about six holes 34 are provided per winding.

In the present embodiment, the holes are circular and arranged in regular spacing from one another. The form, distribution and number of perforations is selected such that sufficient stability of the body is maintained, although numerous locations are present for growth through the body.

As illustrated with the arrow in FIG. 1, bone material can grow into the interior of the body 12 through the numerous perforations 32 or holes 34. This is also possible at the corresponding end openings of the central channel 14 in the region of the head 16 or the penetrating end 18.

Figure 2:
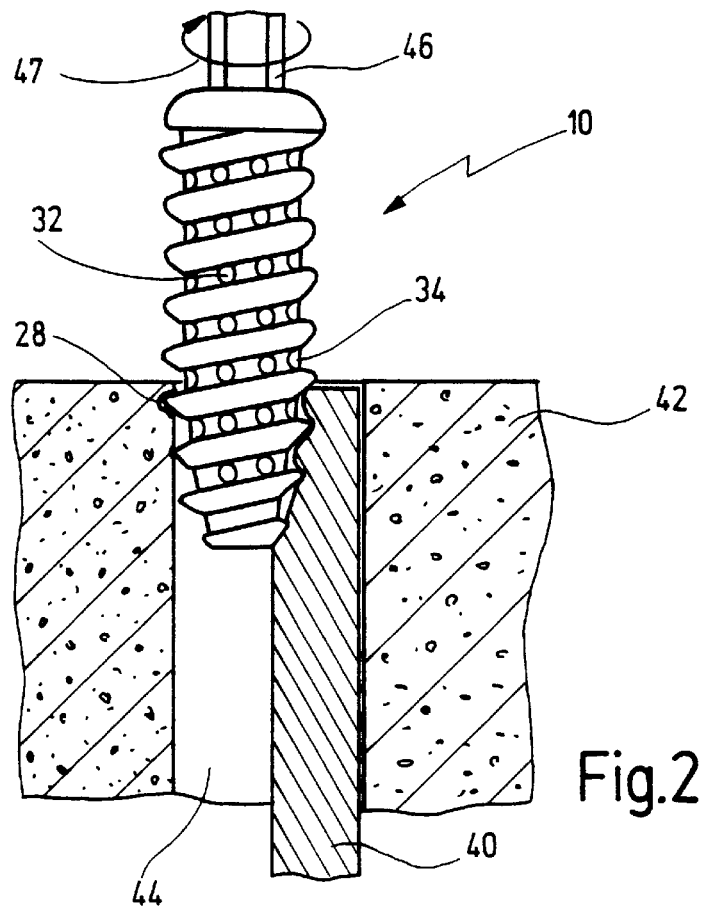
FIG. 2 shows a partial cross-section where the fixation element is just beginning to be driven into a bore channel in a bone with a tool for anchoring a transplant.
Figure 3:
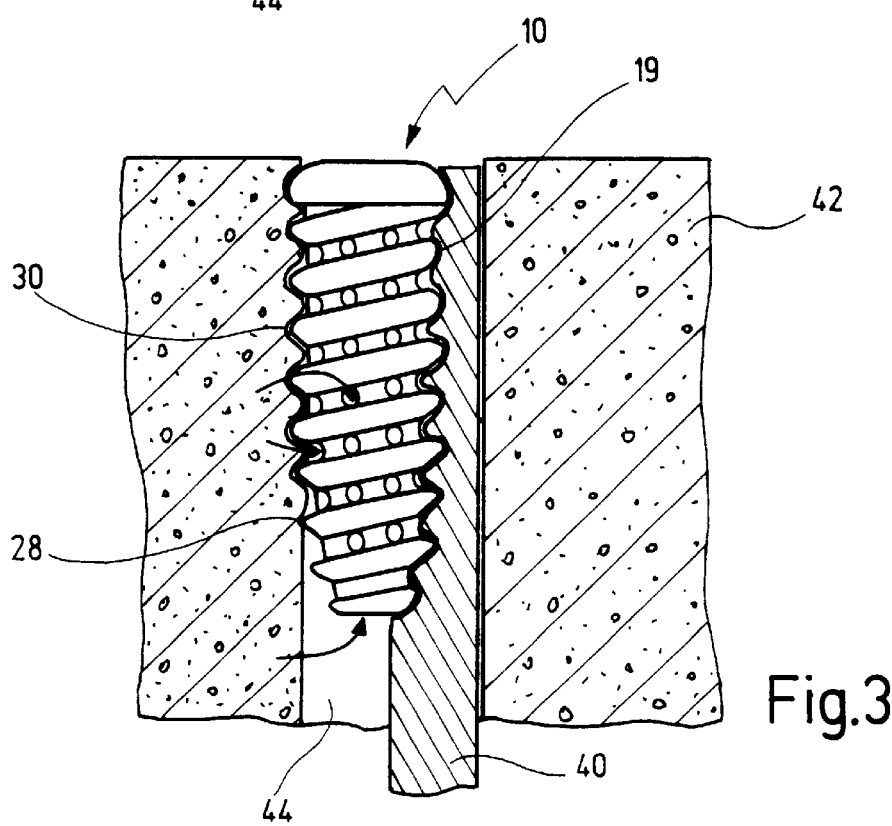
FIG. 3 shows an illustration comparable to FIG. 2 after completely inserting the fixation element with the anchored transplant.

The operating procedure with an interference screw is illustrated in FIGS. 2 and 3. An opening in the form of a channel is provided in a bone 42, in which a tendon or ligament transplant 40 is to be anchored. The diameter of the channel 42 is selected such that the transplant 40 or an end thereof can be placed in the channel 44.

When replacing a cruciate ligament, corresponding channels 44 are provided in the femur and also in the tibia and the transplant is anchored in both bones, as shown for example in FIG. 1 of the mentioned article in OP-Journal 14, 1998, et seq.

After placing the transplant 40 in the channel 44, the interference screw 11 is placed such that its penetrating end 18 lies between the inner wall of the channel 44 and the outermost end of the transplant 40. Placing and inserting the screw is made easier by the tapering in the region of the penetrating end 18.

A tool 46 is applied to the head 16, whose outer contour corresponds to the cross-section of the interior of the channel 14, for example a sexangular cross-section. By rotating the tool 46, as shown by the arrow 47, the interference screw 11 can be inserted.

FIG. 2 shows the situation in which the sharp edges 28 of the threading 20 in the region of the penetrating end 18 are just coming into contact with the inner wall of the channel 44, i.e. with the bone material.

When rotating the interference screw 11, the sharp edges 28 cut a relatively narrow, sharp, spiral path into the inner side of the channel 44. When turning the screw 11 further, the following blunt threads follow in the inner threading previously cut by the sharp edges 28, expand the inner threading and provide for the actual radial compression. The blunt portions of the threading, as shown in the right side of FIG. 3, penetrate correspondingly deeply and securely into the transplant 40.

With time, the bone material can now grow into the interior of the body 12 through the perforations 32 or the holes 34. The interior can be filled with bone material, for example bone slurry or bone parts, for example taken from the pelvic crest region of the patient. A fixed composite of bone material with the interior of the interference screw is soon formed, for example after six to eight weeks. With time, the biodegradable material degrades so that further bone material can grow into the resulting empty spaces.

With this advantageous configuration, the time for biodegradation need not be correlated with the rate of bone growth, which can take place much faster since the bone material has sufficient space available due to the perforations 32. Thus a three-dimensional interconnected bone structure is formed even before or during the biological degradation.

What is claimed is:

1. Interference screw for anchoring a tendon transplant within a bore channel in a bone by laterally urging said tendon transplant within said bore channel via said interference screw against a wall of said bore channel, comprising
   - a rigid body made of biodegradable material, said body having an outer side and a hollow interior surrounded by a wall of said body,
   - a threading provided at said outer side of said rigid body for anchoring with said wall of said bore,
   - numerous holes passing through said wall of said body, said holes are provided between said threading in said body, and
   - wherein said screw body tapers in a penetrating end region extending from a penetrating end to a maximum core diameter, said tapering penetrating end region having at least one winding of said threading.

2. The interference screw of claim 1, wherein no holes are provided up until a first complete winding in said penetrating end region.

3. A method for anchoring a tendon transplant within a bore channel in a bone comprising the steps of:
   providing a bore channel in a bone,
   placing a tendon transplant within said bore channel, said tendon transplant having an outer diameter smaller than a diameter of said bore channel,
   screwing an interference screw into a space between said bore channel and said tendon transplant for laterally urging said tendon transplant between said interference screw and said bore channel, said interference screw comprising:
   a rigid body made of biodegradable material, said body having an outer side and a hollow interior surrounded by a wall of said body,
   a threading provided at said outer side of said rigid body for anchoring with said wall of said bore,
   numerous holes passing through said wall of said body, said holes are provided between said threading in said body, and
   wherein said screw body tapers in a penetrating end region extending from a penetrating end to a maximum core diameter, said tapering penetrating end region having at east one winding of said threading.

* * * * *